US00PP23687P2

(12) United States Plant Patent
Bradford

(10) Patent No.: US PP23,687 P2
(45) Date of Patent: Jun. 25, 2013

(54) INTERSPECIFIC TREE NAMED 'PLUMSWEET XV'

(50) Latin Name: ***Prunus* sp.**
Varietal Denomination: Plumsweet XV

(76) Inventor: Lowell Glen Bradford, Le Grand, CA (US)

( * ) Notice: Subject to any disclaimer, the term of this patent is extended or adjusted under 35 U.S.C. 154(b) by 61 days.

(21) Appl. No.: 13/374,016

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP19,591 P2 12/2008 Bradford

*Primary Examiner* — Annette Para

(57) ABSTRACT

The present invention relates to an interspecific tree and more particularly to a new and distinct variety broadly characterized by a large size, vigorous, hardy, and productive tree. Being self-unfruitful, the present variety requires cross pollination from an apricot, interspecific, or plum that blooms during the mid season. The present variety's abundance of blossoms and pollen entices strong bee activity to facilitate pollination. The fruit matures under the ecological conditions described during mid September, with first picking on Sep. 18, 2011, and will hang on the tree for about fifteen more days. The fruit is uniformly large in size, red mottled over a yellow background in skin color, clingstone in type, globose in shape, yellowish orange to red in flesh color, firm and crisp in texture, and very good in flavor.

1 Drawing Sheet

Botanical classification: *Prunus* sp.
Varietal denomination: 'PLUMSWEET XV'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Plumsweet XV'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2003 one such house containing an unpatented purple plum, code named '42P1156', was crossed by me in this manner. To pollinate this purple plum, I selected bouquets from several sources of apricot and interspecific hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2006 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is most similar to its sister variety 'Plumred X' (U.S. Plant Pat. No. 19,591) interspecific tree by being self-unfruitful yet productive, by blooming in the mid season, and producing fruit that is globose in shape, firm, crisp, juicy, sweet and very good in flavor, but is distinguished therefrom by producing fruit that is a yellow to red two-tone instead of full red in flesh color, that has shown to be less prone to cracking, and that matures about ten day later.

SUMMARY OF VARIETY

The present interspecific variety is characterized by a large size, vigorous, hardy, and productive tree. Being self-unfruitful, the present variety requires cross pollination from an apricot, interspecific, or plum that blooms during the mid season. The present variety's abundance of blossoms and pollen entices strong bee activity to facilitate pollination. The fruit matures under the ecological conditions described during mid September, with first picking on Sep. 18, 2011, and will hang on the tree for about fifteen more days. The fruit is uniformly large in size, red mottled over a yellow background in skin color, clingstone in type, globose in shape, yellowish orange to red in flesh color, firm and crisp in texture, and very good in flavor.

DRAWING

The accompanying photograph consists of four whole fruits positioned to display the characteristics of the skin color and form, a half fruit divided to reveal the flesh and stone, typical leaves, a tip shoot growth, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of shipping ripe on Sep. 21, 2011, on the original tree during its eighth growing season. The flower and bud descriptions were developed during the previous blooming season. All major color code designations are by reference to the Inter-Society Color Council, National Bureau of Standards. Common color names are also used occasionally.

PARENTAGE

Seed parent: '42P1156' plum (unpatented).
Pollen parent: Unknown.

TREE

Size: Large, reaching and maintaining a height of 14' [4.27 m.] and a spread of 7' [2.13 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid seasonal blooming apricot, interspecific, or plum, such as 'Blackred IV' interspecific tree (U.S. Plant Pat. No. 20,832).

Bearing: Regular bearer.

Trunk:

- *Size*.—Large, reaching a maximum diameter of 4½" [114.3 mm.] after the eight growing season.
- *Texture*.—Medium.
- *Bark color*.—Dark grayish brown [62. d.gy.Br] with Light yellowish brown [76. l.yBr] crevices present.
- *Lenticels*.—Approximate Number Per Square Inch: 12. Color: Light yellowish brown [76. l.yBr]. Size: ⅛" [3.2 mm.] to ¼" [6.4 mm.]. Shape: Eye-shaped, elongated.

Branches:

- *Size*.—Main scaffold is 3¼" [82.6 mm.] measured 12" above first hanger. Maximum diameter of first hanger is 1" [25.4 mm.].
- *Texture*.—Smooth on first and second year wood, increasing roughness with age.
- *Color*.—2nd Year Wood: Strong yellowish brown [74. s.yBr] with Strong yellow green [117. s.YG] permeating through. Older Wood: A Dark grayish brown [62. d.gy.Br] and Dark brown [59. d.Br] variegation with Light yellowish brown [76. l.yBr] crevices present.
- *Lenticels*.—Number Per Square Inch: About 60 on second year wood. Color: Light yellowish brown [76. l.yBr]. Average Size: 1/64" [0.4 mm.]. Shape: Elongated, rectangular.

Leaves:

- *Size*.—Large. Average Length: 4⅝" [117.5 mm.]. Average width: 2 1/16" [52.4 mm.].
- *Arrangement*.—Alternate.
- *Thickness*.—Medium.
- *Form*.—Elliptical.
- *Apex*.—Acuminate.
- *Base*.—Some rounded, some acute with an average base angle of 65 degrees.
- *Surface*.—Smooth.
- *Color*.—Dorsal Surface: Moderate olive green [125. m.OlG]. Ventral Surface: Deep yellow green [118. deep YG].
- *Margin*.—Finely serrate.
- *Venation*.—Pinnately net veined.
- *Petiole*.—Average Length: 5/16" [7.9 mm.]. Average Thickness: 1/16" [1.6 mm.]. Color: Brilliant yellow green [116. brill.YG].
- *Stipules*.—Number: 2 per leaf, up to 6 per growing tip. Average Length: ¼" [6.4 mm.]. Color: Light yellow green [119. l.YG] becoming Moderate brown [58. m.Br] with age.
- *Glands*.—Number: 3 to 4 per leaf. Position: Alternately positioned at petiole and base of leaf blade. Size: Medium. Form: Globose. Color: Light yellow green [119. l.YG] becoming Grayish brown [61. gy.Br] with age.
- *Leaf buds*.—Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.

- *Average flower diameter*.—1" [25.4 mm.].
- *Number of petals*.—Five, no double blossoms observed.
- *Petal shape*.—Oval to circular.
- *Petal margin*.—Entire, somewhat wavy.
- *Average petal diameter*.—7/16" [11.1 mm.].
- *Average petal length*.—½" [12.7 mm.].
- *Petal apex*.—Rounded.
- *Petal base*.—Obtuse.
- *Petal color*.—White [263. White] on both sides.
- *Anther color*.—Moderate orange yellow [71. m.OY].
- *Stigma color*.—Brilliant greenish yellow [98. brill.gY].
- *Sepal color*.—Light yellow green [119. brill.YG].
- *Sepal length*.—5/32" [4.0 mm.].
- *Sepal width*.—5/32" [4.0 mm.].
- *Sepal apex*.—Rounded to elliptical to match the width and length.
- *Sepal margin*.—Fairly smooth to the naked eye, slightly serrate when magnified.

*Average pistil length.*—5/8" [15.9 mm.], longer than normal.
*Average stamen length.*—7/16" [11.1 mm.].
*Fragrance.*—Moderate.
*Pollen production.*—Abundant, very bee enticing.
*Blooming period.*—Medium, two days after 'Black Amber' plum (unpatented).
*Onset of bloom.*—One percent on Feb. 27, 2011.
*Date of full bloom.*—Mar. 7, 2011.
*Duration of bloom.*—One to two weeks, dependent on ambient temperature.
*Bloom density.*—Very heavy.
*Number per cluster.*—2 to 10, average 6.

FRUIT

Maturity when described: Shipping ripe, Sep. 21, 2011.
Date of first picking: Sep. 18, 2011.
Date of last picking: Oct. 2, 2011.
Size: Uniform, Large.
*Average diameter axially.*—2¾" [69.9 mm.].
*Average diameter across cheek plane.*—2⅝" [66.7 mm.].
*Average diameter across suture plane.*—2¾" [69.9 mm.].
*Typical weight.*—6.6 ounces [187 grams].
Form: Uniform, globose, symmetrical.
*Longitudinal section form.*—Round to slightly oblong.
*Transverse section through diameter.*—Round.
Suture: An inconspicuous line located in a shallow groove extending from the base to the apex, ending in a small depression.
Ventral surface: Rounded, very slightly lipped toward apex and base.
Lips: Fairly equal.
Cavity: Rounded, suture showing on one side.
*Depth.*—7/16" [11.1 mm.].
*Breadth.*—¾" [19.1 mm.].
Base: Slightly truncate, cordate if viewed parallel to the suture.
Apex: Rounded.
Pistil point: An inconspicuous dot.
Stem: Medium.
*Average length.*—7/16" [11.1 mm.].
*Average width.*—⅛" [3.2 mm.].
Skin:
*Thickness.*—Medium.
*Surface.*—Smooth.
*Tenacity.*—Tenacious to the flesh.
*Astringency.*—Slight.
*Tendency to crack.*—Somewhat resistant to growth cracks, with only a few minor shoulder cracks observed.
*Color.*—Moderate yellow [87. m.Y] with Deep reddish orange [36. deep rO] mottling throughtout and Dark grayish red [20. d.gy.R] freckling somewhat stronger toward the apex.
*Bloom.*—Abundant.
Flesh:
*Color.*—Light orange yellow [70. l.OY] with a Very red [11. v.R] ring toward the skin.
*Surface of pit cavity.*—Covered with Light orange yellow [70. l.OY] and Deep red [13. deep R] broken fibers when twisted from the stone.
*Amygdalin.*—Moderate.
*Juice.*—Moderate, rich.
*Texture.*—Firm, crisp.
*Fibers.*—Few, fine, tender.
*Ripens.*—Earliest toward the apex.
*Flavor.*—A balanced blend of acid and sugar, typically 20 brix.
*Aroma.*—Moderate.
*Eating quality.*—Very good.

STONE

Type: Clingstone.
Form: Oval.
Hilum: Narrow.
Base: Straight.
Apex: Acute, with a sharp 1/16" [1.6 mm.] tip.
Sides: Equal.
Surface: Regularly furrowed throughout.
External color of stone: Light grayish yellowish brown [79. l.gy.yBr].
Pit wall color when cracked: Moderate orange yellow [71. m.OY].
Cavity surface color: Deep yellowish brown [75. deep yBr].
Average pit wall thickness: ⅛" [3.2 mm.].
Average width: 7/16" [11.1 mm.].
Average length: ⅞" [22.2 mm.].
Average breadth: ⅜" [9.5 mm.].
Tendency to split: None observed.
Kernel:
*Form.*—Oval.
*Skin color.*—Dark orange yellow [72. d.OY] when first removed.
*Pellicle color.*—Grayish yellowish brown [80. gy.yBr].
*Vein color.*—Moderate yellowish brown [77. m.yBr].
*Taste.*—Bitter.
*Viable.*—Yes.
*Average width.*—7/16" [11.1 mm.].
*Average length.*—5/8" [15.9 mm.].
*Amygdalin.*—Moderate.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is most similar to its sister variety 'Plumred X' (U.S. Plant Pat. No. 19,591) interspecific tree by being self-unfruitful yet productive, by blooming in the mid season, and producing fruit that is globose in shape, firm, crisp, juicy, sweet and very good in flavor, but is distinguished therefrom by producing fruit that is a yellow to red two-tone instead of full red in flesh color, that appears to be less prone to cracking, and that matures about ten day later.

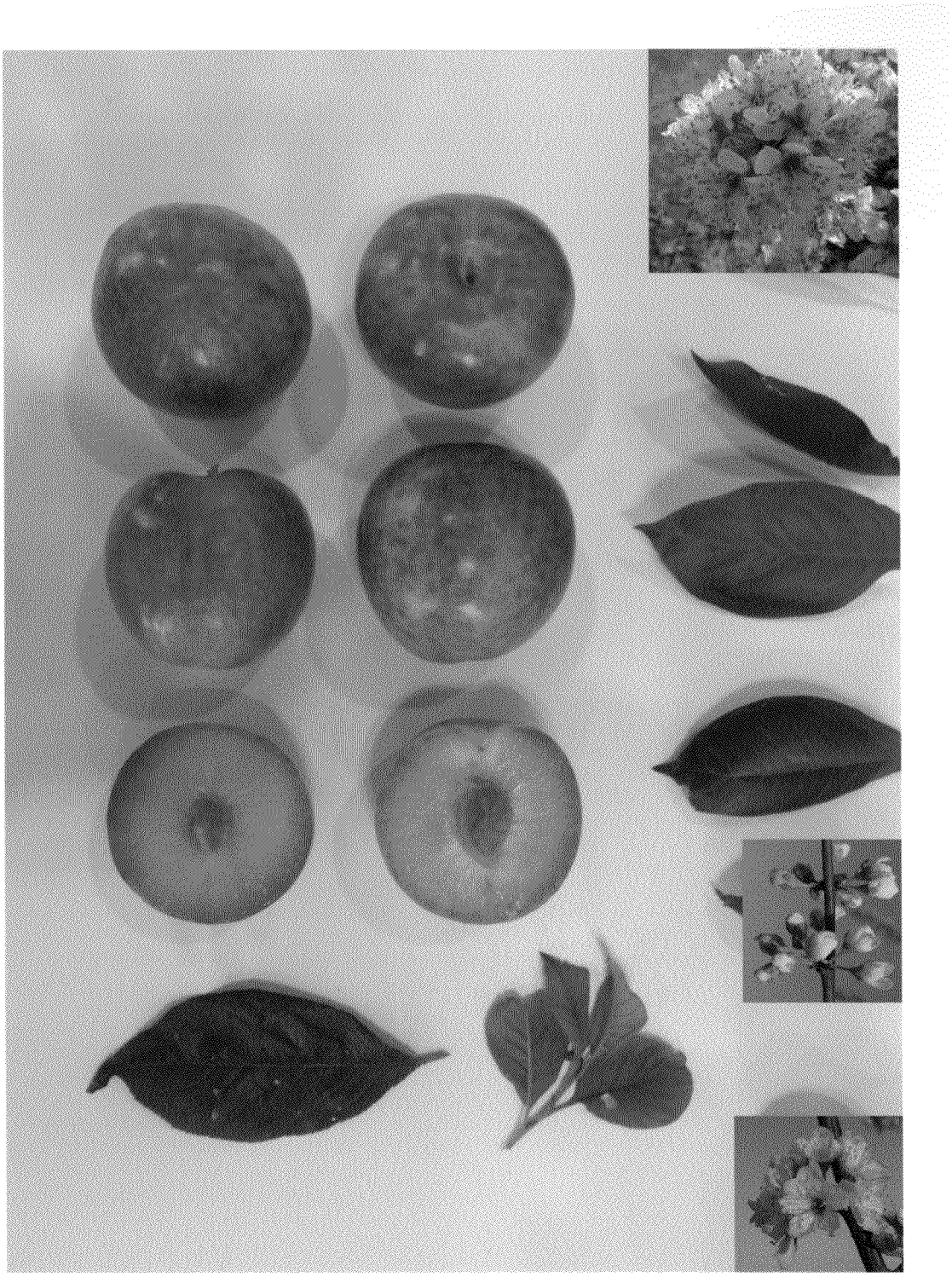

* * * * *